(12) United States Patent
Dalko et al.

(10) Patent No.: US 6,541,507 B1
(45) Date of Patent: Apr. 1, 2003

(54) INDOLECARBOXYLIC COMPOUNDS FOR INDUCING/STIMULATING HAIR GROWTH AND/OR RETARDING HAIR LOSS

(75) Inventors: Maria Dalko, Gif S/Yvette (FR); Jean-Baptiste Galey, Aulnay-Sous-Bois (FR); Bruno Bernard, Neuilly sur Seine (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/617,106

(22) Filed: Jul. 14, 2000

(30) Foreign Application Priority Data

Jul. 16, 1999 (FR) .............................. 99 09268

(51) Int. Cl.[7] .......................... A61K 31/40; A61K 7/00; A61K 31/70; C07D 411/00; C07D 209/52; C09K 3/00
(52) U.S. Cl. .......................... 514/429; 424/401; 514/38; 548/454; 548/516; 252/380
(58) Field of Search .......................... 252/380; 548/454, 548/516; 514/38, 429; 424/401

(56) References Cited

U.S. PATENT DOCUMENTS

| | | | |
|---|---|---|---|
| 5,342,547 A | * | 8/1994 | Konya et al. ................ 252/380 |
| 5,767,139 A | * | 6/1998 | Maw et al. ................... 514/38 |
| 5,912,357 A | * | 6/1999 | Blagg et al. ................. 548/454 |

FOREIGN PATENT DOCUMENTS

| | | |
|---|---|---|
| EP | 0470490 | 2/1992 |
| EP | 0 565 417 | * 10/1993 |
| WO | 99/07351 | 2/1999 |
| WO | 99/12905 | 3/1999 |

OTHER PUBLICATIONS

Black et al., Aust. J. Chem., 1986, 39, 15–20.*
Prager et al., Aust. J. Chem., 1996, 49, 1315–1323.*
Tani et al., Heterocycles, 1992, 34(12), 2349–2362.*
Allen et al., Synth. Comm., 1992, 22(14), 2077–2102.*
D.A. Holt et al: "Benzophenone– and indolecarboxylic acids: potent type–2 specific inhibitors of human steroid 5alpha–reductasel", Journal Lof Medicinal Chemistry, vol. 38, No. 1, 1995, pp. 13–15, XP002068506, Washington US p. 13, colonne de gauche, lines 1–11, Table 2.

* cited by examiner

Primary Examiner—Sreeni Padmanabhan
Assistant Examiner—Michael A. Willis
(74) Attorney, Agent, or Firm—Burns, Doane, Swecker & Mathis, L.L.P.

(57) ABSTRACT

Indolecarboxylic acid compounds and derivatives thereof, notably 4,6-dimethoxyindole-2-carboxylic acid and derivatives thereof, are especially useful for inducing/stimulating mammalian hair growth and/or preventing/retarding mammalian hair loss.

21 Claims, No Drawings

INDOLECARBOXYLIC COMPOUNDS FOR INDUCING/STIMULATING HAIR GROWTH AND/OR RETARDING HAIR LOSS

CROSS-REFERENCE TO PRIORITY APPLICATION

This application claims priority under 35 U.S.C. § 119 of FR-99/09268, filed Jul. 16, 1999, hereby expressly incorporated by reference.

CROSS-REFERENCE TO COMPANION APPLICATION

Copending and commonly assigned application Ser. No. 09/617,039, filed Jul. 14, 2000, now U.S. Pat. No. 6,335,359.

BACKGROUND OF THE INVENTION

1. Technical Field of the Invention

The present invention relates to the administration of an effective amount of 4,6-dimethoxyindole-2-carboxylic acid or derivative or composition comprised thereof, to induce and/or stimulate hair growth and/or to prevent hair loss.

2. Description of the Prior Art

In human subjects, the growth and renewal of the hair are principally determined by the activity of the hair follicles. This activity is cyclic and essentially comprises three phases, i.e., the anagenic phase, the catagenic phase and the telogenic phase.

The active anagenic phase, or growth phase, which lasts for several years and during which the hair becomes longer, is followed by a very short and transient catagenic phase which lasts a few weeks, and then a rest or quiescent phase, known as the telogenic phase, which lasts a few months.

At the end of the rest period, the hair falls out and another cycle begins. The head of hair is thus under constant renewal, and out of the approximately 150,000 hairs on a human head of hair, at any given moment, approximately 10% of them are at rest and will thus be replaced within a few months.

However, different causes can lead to a considerable, temporary or permanent, loss of hair. Alopecia is essentially due to a disruption in hair renewal which gives rise, in a first stage, to an acceleration of the frequency of the cycles, at the expense of the quality of the hair and then at the expense of its quantity. A gradual depletion of the head of hair takes place by regression of the so-called "terminal" hairs at the downy stage. Regions are preferentially affected, in particular the temples or frontal bulbs in men, and in women diffuse alopecia of the vertex is observed.

The term "alopecia" is generic to the entire family of afflictions of the hair follicle, the final consequence of which is the partial or general permanent loss of the hair. In a large number of cases, early loss of the hair occurs in genetically predisposed individuals and especially is prevalent in men. This ie more particularly the case as regards androgenetic or androgenic or even androgeno-genetic alopecia.

Active agents for suppressing or reducing alopecia, and in particular for inducing or stimulating hair growth or reducing hair loss, have long been considered desiderata in the cosmetics and pharmaceutical industries.

In this respect, a large number of very diverse active compounds have already been proposed for such purposes, for example, 2,4-diamino-6-piperidino-pyrimidine 3-oxide or "Minoxidil" as described in U.S. Pat. Nos. 4,139,619 and 4,596,812, or the many derivatives thereof, such as those described, for example, in EP-0,353,123, EP-0,356,271, EP-0,408,442, EP-0,522,964, EP-0,420,707, EP-0,459,890 and EP-0,519,819.

Specific compounds of the indolecarboxylic family, such as those described in WO-A-99/12905, have also been proposed for their ability to induce and/or stimulate hair growth and/or to prevent hair loss.

These compounds exhibit pronounced inhibitory activity on type I and type II 5α-reductases, which, according to the theory which considers that these proteins are involved in hair loss, makes them excellent candidates as active principles for inducing and/or stimulating hair growth and/or for preventing hair loss.

However, 5α-reductases are not exclusively present in the hair follicles, and the value of providing compounds suited for inducing and/or stimulating hair growth and/or of preventing hair loss, but which have no activity on type I and II 5α-reductases, consequently, can readily be appreciated.

SUMMARY OF THE INVENTION

It has now surprisingly and unexpectedly been determined that 4,6-dimethoxyindole-2-carboxylic acid and derivatives thereof have the property of inducing and/or stimulating hair growth and/or of preventing hair loss, but do not exhibit any activity on type I and type II 5α-reductases.

Briefly, the present invention features cosmetic/dermatological compositions comprising a therapeutically effective amount of at least one compound having the structural formula (I):

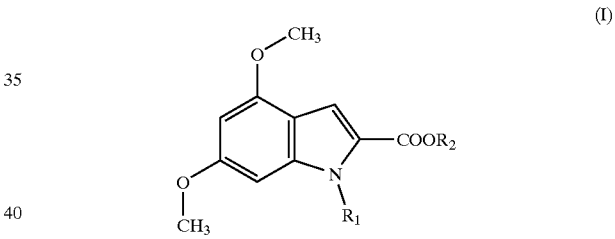

in which $R_1$ and $R_2$, which may be identical or different, are each a hydrogen atom; a $C_1$–$C_6$ alkyl radical, optionally substituted with an —OH, —$NHR_3$, —SH, —COOH or —$COOR_3$ radical, in which $R_3$ is a linear or branched $C_1$–$C_4$ alkyl radical; a $C_7$–$C_{12}$ aralkyl radical; or a radical —$CHR_4R_5$, wherein $R_4$ and $R_5$, which may be identical or different, are each a hydrogen atom, an optionally substituted phenyl radical, or a 5- or 6-membered heterocycle; the acylated derivatives or the physiologically acceptable salts thereof, either singly or in any admixture in any proportion; said compound and/or said compositions being well suited to induce and/or stimulate hair growth and/or to prevent hair loss.

DETAILED DESCRIPTION OF BEST MODE AND SPECIFIC/PREFERRED EMBODIMENTS OF THE INVENTION

More particularly according to the present invention, the subject compounds exhibit marked utility as active principles for inducing and/or stimulating hair growth and/or for preventing hair loss.

It was hitherto unknown to administer such compounds for combating hair loss.

According to the invention, by the term "heterocycle" is preferably intended a ring optionally including one or more nitrogen and/or oxygen atoms, and particularly pyridine, imidazole, tetrahydrofuran or furan. One heterocycle which is particularly preferred according to the invention is pyridine.

By the expression "$C_1$–$C_4$ alkyl radical" are intended linear or branched acyclic radicals having from 1 to 4 carbon atoms, derived from the removal of a hydrogen atom from a hydrocarbon molecule, and in particular methyl, ethyl, propyl, isopropyl, butyl, isobutyl or tert-butyl radicals.

By the expression "$C_7$–$C_{12}$ aralkyl radical" are preferably intended alkylaryl radicals containing from 7 to 12 carbon atoms, in which definition the term "aryl" connotes an aromatic ring containing 5 or 6 carbon atoms or an aromatic heterocycle containing 5 or 6 atoms. According to the invention, the aralkyl radical is preferentially $C_7$–$C_{10}$. One aralkyl radical which is particularly preferred according to the invention is the benzyl radical.

And by the expression "optionally substituted phenyl radical" is preferably intended a phenyl radical optionally substituted with a cyano (—CN) group, a trifluoromethyl (—$CF_3$) group, a methoxy (—O—$CH_3$) radical or a halogen atom. The halogen atom can be selected from among chlorine, bromine, fluorine and iodine. One substituted phenyl radical which is particularly preferred according to the invention is a phenyl radical substituted with a trifluoromethyl (—$CF_3$) group.

In one preferred embodiment of the invention, $R_1$ is a hydrogen atom or a methyl or ethyl radical.

In another preferred embodiment of the invention, $R_2$ is a hydrogen atom or a methyl radical.

And in a very preferred embodiment of the invention, $R_1$ and $R_2$ are each a hydrogen atom.

Exemplary compounds of formula (I) include:
4,6-dimethoxyindole-2-carboxylic acid;
methyl 4,6-dimethoxyindole-2-carboxylate;
N-methyl-4,6-dimethoxyindole-2-carboxylic acid;
methyl N-methyl-4,6-dimethoxyindole-2-carboxylate;
N-ethyl-4,6-dimethoxyindole-2-carboxylic acid.

Among these compounds, that most particularly preferred is 4,6-dimethoxyindole-2-carboxylic acid.

According to the invention, the subject compounds can be used alone or as a mixture.

It will of course be appreciated that the effective amount of compound to be administered corresponds to the amount required to elicit the desired result. One skilled in this art is thus capable of evaluating this effective amount, which depends on the nature of the compound and on the person thus treated. To provide an order of magnitude, in the compositions according to the invention the compound of formula (I) is typically present at a concentration ranging from 0.3% to 30% by weight relative to the total weight of the composition and preferably from 0.5% to 20%.

According to the invention, the compounds of formula (I) can be formulated into any suitable medium (vehicle, diluent or carrier) for cosmetic or pharmaceutical applications. The compounds of formula (I) are preferentially formulated into compositions for cosmetic application.

The physiologically acceptable medium in which the active agent is formulated according to the invention is anhydrous or aqueous. By the expression "anhydrous medium" is intended a solvent medium containing less than 1% water. This medium is a solvent or a mixture of solvents selected more particularly from among $C_2$–$C_4$ lower alcohols such as ethyl alcohol, alkylene glycols such as propylene glycol, and alkylene glycol alkyl ethers or dialkylene glycol alkyl ethers, the alkyl or alkylene radicals of which have from 1 to 6 carbon atoms. By the expression "aqueous medium" is intended a medium of water or of a mixture of water and another physiologically acceptable solvent, selected in particular from among the organic solvents indicated above. In this latter instance, when these other solvents are present, they constitute approximately 5% to 95% by weight of the composition.

The physiologically acceptable medium can also contain other adjuvants and additives usually formulated into cosmetics or pharmaceuticals, such as surfactants, thickeners or gelling agents, cosmetic agents, preservatives, and acidifying and basifying agents that are well known to the prior art, and in amounts that are sufficient to provide the desired presentation form, in particular a more or less thickened lotion, a gel, an ointment, a milk, an emulsion or a cream. The composition can optionally be provided in a form pressurized as an aerosol or vaporized from a pump-dispenser bottle.

The subject active agents can also be formulated in combination with compounds for further improving the activity on hair growth and/or on preventing hair loss, which have already been described for such activity.

Among these, more particularly exemplary are:
(a) nicotinic acid esters, in particular tocopheryl nicotinate, benzyl nicotinate and $C_1$–$C_6$ alkyl nicotinates such as methyl or hexyl nicotinate;
(b) pyrimidine derivatives, such as 2,4-diamino-6-piperidinopyrimidine 3-oxide or "Minoxidil" described in U.S. Pat. Nos. 4,139,619 and 4,596,812;
(c) agents for promoting hair regrowth, such as those described in the European patent application published under No. 0,648,488 assigned to the assignee hereof;
(d) antibacterial agents such as macrolides, pyranosides and tetracyclines, and in particular erythromycin;
(e) calcium antagonists such as Cinnarizine, Diltiazem, Nimodipine and Nifedipine;
(f) hormones, such as estriol or analoges thereof, or thyroxine and salts thereof;
(g) steroidal anti-inflammatory agents, such as corticosteroids (for example hydrocortisone);
(h) antiandrogenic agents, such as oxendolone, spironolactone, diethylstilbestrol and flutamide;
(i) steroidal or non-steroidal 5α-reductase inhibitors such as finasteride;
(j) potassium agonists such as cromakalim and nicorandil.

Other compounds are also representative additives, for example, diazoxide, spiroxazone, phospholipids such as lecithin, linoleic acid, linolenic acid, salicylic acid and derivatives thereof described in FR-2,581,542, for instance salicylic acid derivatives bearing an alkyl radical having from 2 to 12 carbon atoms in position 5 of the benzene ring, hydroxycarboxylic or ketocarboxylic acids and esters thereof, lactones and the corresponding salts thereof, anthralin, carotenoids, eicosatetraenoic and eicosatrienoic acids or esters and amides thereof, vitamin D and derivatives thereof, and extracts of plant or bacterial origin.

The compositions comprising at least one compound of formula (I) can also be formulated in liposomal form, as described, in particular, in WO-94/22468, filed Oct. 13, 1994 by the company Anti-Cancer Inc. Thus, the compound encapsulated in the liposomes can be delivered selectively to the hair follicles.

The cosmetic compositions according to the invention can be topically applied onto the alopecic regions of the scalp and hair of an individual, and are optionally maintained in contact for several hours and then optionally rinsed therefrom. For example, the compositions containing an effective amount of at least one compound as described above can be applied in the evening, maintained in contact throughout the night and optionally shampooed out in the morning. These applications can be repeated daily for one or more months depending on the particular individual.

Thus, the present invention also features a cosmetic regime/regimen for treating the hair and/or the scalp, comprising topically applying onto the hair and/or the scalp a cosmetic composition which comprises an effective amount of at least one compound of formula (I), in maintaining this composition in contact with the hair and/or the scalp, and optionally rinsing same therefrom.

Such regime/regimen has the characteristics of a cosmetic methodology since it improves the aesthetics of the hair by rendering it more vigorous and better in appearance.

In order to further illustrate the present invention and the advantages thereof, the following specific examples are given, it being understood that same are intended only as illustrative and in nowise limitative.

EXAMPLE 1

Comparative Evaluations of the Inhibitory Effect of 4,6-Dimethoxyindole-2-carboxylic Acid and of 5-Methoxy-6-benzyloxyindole-2-carboxylic Acid on Type I and Type II 5α-Reductases The coding sequences (complementary deoxyribonucleic acids: cDNAs) of 5α-reductase I and of 5α-reductase II were cloned into the eukaryotic expression vector pSG5 (Stratagene). The enzymes were overexpressed after transient transfection of COS7 cells (ATCC, CRL 1651). The 5α-reductase I and 5α-reductase II cDNAs were obtained by reverse transcription and polymerase chain reaction (PCR) using specific primers from human testicle total RNA (marketed by Clontech).

The primers (SEQ ID NOS.: 1 and 2) used to obtain the 5α-reductase I cDNA were:

+strand: 5'CCCAGCCCTGGCGATGGCAAC 3',
−strand: 5'GGATATTCAACCTCCATTTCAG 3'.

The primers (SEQ ID NOS.: 3 and 4) used to obtain the 5α-reductase II cDNA were:

+strand: 5'GCGATGCAGGTTCAGTG 3',
−strand: 5'ATTGTGGGAGCTCTGCT 3'.

The 5α-reductase I cDNA obtained was inserted, by standard genetic engineering techniques, into the BamHI site of pSG5 and the 5α-reductase II cDNA obtained was inserted into the EcoRI site (see Maniatis et al., *Molecular Cloning*, Cold Spring Harbor, 1989).

The positive clones (recombinants) were identified by the technique of hybridization with a cold probe (Plex luminescent kits, Millipore) and mapped by enzymatic digestions and partial sequencing. After transient transfection, the COS7 cells were lysed in a 10 mM Tris-HCl, pH=7/150 mM KCl/1 mM EDTA buffer by 3 cycles of freezing/thawing. The homogenate was centrifuged at 100,000×g for 1 hour. The pellets containing the 5α-reductase I or 5α-reductase II were taken up in a 40 mM, pH 6.5 phosphate buffer or 40 mM, pH 5.5 citrate buffer for 5α-reductase I or 5α-reductase II, respectively.

5 μg of proteins thus obtained were incubated in a 96-well plate (NUNC) in the presence of 1 nM $^{14}$C-testerone (Amersham) and 5 mM nicotinamide adenosine dinucleotide phosphate, reduced form (NADPH) (Sigma) in the corresponding buffer (40 mM, pH 6.5 phosphate buffer or 40 mM, pH 5.5 citrate buffer for 5α-reductase I or 5α-reductase II, respectively) for 50 minutes at 37° C. after addition of the test products. The test products were added at concentrations from $10^{-4}$, M to $10^{-10}$ M, diluted in 40 mM, pH 6.5 phosphate buffer or 40 mM, pH 5.5 citrate buffer for 5α-reductase I or 5α-reductase II, respectively.

The reaction mixtures were then deposited directly on a silica plate (HPTLC, 60F 254, Merck) and subjected to chromatography (solvent=10% diethyl ether, 90% dichloromethane). They were then analyzed by digital autoradiography (Digital Autoradiography, Berthold).

The inhibition of the activity of the isoenzymes was measured by calculating the percentage of dihydrotestosterone formed from $^{14}$C-testosterone relative to an untreated control.

The results obtained are reported in the following Table:

TABLE

| Compound | Type I 5α-reductase IC$_{50}$ (μM) | Type II 5α-reductase IC$_{50}$ (nM) |
|---|---|---|
| 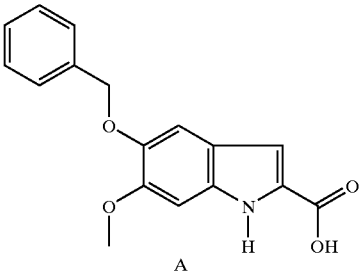 | 1 | 1 |
| 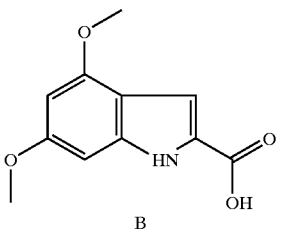 | 50 | >>50 (μM) |

A: 5-methoxy-6-benzyloxyindole-2-carboxylic acid
B: 4,6-dimethoxyindole-2-carboxylic acid 4,6-Dimethoxyindole-2-carboxylic acid exhibited no inhibitory effect on the 5α-reductases.

EXAMPLE 2

The following specific compositions according to the invention were formulated via conventional cosmetics/pharmacy techniques.

Lotion:

| | |
|---|---|
| 4,6-Dimethoxyindole-2-carboxylic acid | 5.00 g |
| Propylene glycol | 10.00 g |
| Isopropyl alcohol | qs 100.00 g |

1 ml of this lotion is applied to the scalp, at a frequency of once or twice a day.

Lotion:

| | |
|---|---|
| 4,6-Dimethoxyindole-2-carboxylic acid | 1.00 g |
| Propylene glycol | 30.00 g |
| Ethyl alcohol | 40.00 g |
| Water | qs 100.00 g |

This lotion is applied to the scalp once or twice a day, at a rate of 1 ml per application.

Thickened lotion:

| | |
|---|---|
| 4,6-Dimethoxyindole-2-carboxylic acid | 1.00 g |
| Kawain | 2.00 g |
| Klucel G ®* | 3.50 g |
| Ethyl alcohol | qs 100.00 g |

This thickened lotion is applied to the scalp once or twice a day, at a rate of 1 ml per application.

Lotion:

| | |
|---|---|
| 4,6-Dimethoxyindole-2-carboxylic acid | 2.00 g |
| Dowanol PM ®** | 20.00 g |
| Klucel G ®* | 3.00 g |
| Ethyl alcohol | 40.00 g |
| Water | qs 100.00 g |

This thickened lotion is applied to the scalp once or twice a day, at a rate of 1 ml per application.

Lotion:

| | |
|---|---|
| 4,6-Dimethoxyindole-2-carboxylic acid | 1.00 g |
| Propylene glycol | 30.00 g |
| Ethyl alcohol | 40.00 g |
| Water | qs 100.00 g |

This lotion is applied to the scalp once or twice a day, at a rate of 1 ml per application.

*: Hydroxypropylcellulose marketed by Hercules

**: Propylene glycol monomethyl ether marketed by Dow Chemical

While the invention has been described in terms of various specific and/or preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for inducing or stimulating mammalian hair growth and/or retarding mammalian hair loss on a mammalian subject in need of such treatment, comprising topically applying onto the hair and/or scalp of said mammalian subject, a hair growth inducing or stimulating and/or hair loss retarding effective amount of at least one indolecarboxylic acid compound, or ester or salt thereof, said at least one indolecarboxylic acid compound having the structural formula (I):

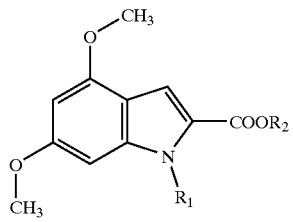

(I)

in which $R_1$ and $R_2$, which may be identical or different, are each a hydrogen atom; a $C_1$–$C_6$ alkyl radical, optionally substituted with an —OH, —$NHR_3$, —SH, —COOH or —$COOR_3$ radical, wherein $R_3$ is a linear or branched $C_1$–$C_4$ alkyl radical; a $C_7$–$C_{12}$ aralkyl radical;

or a radical —$CHR_4R_5$ wherein $R_4$ and $R_5$, which may be identical or different, are each a hydrogen atom, an optionally substituted phenyl radical, or a 5- or 6-membered heterocycle;

or an acylated derivative or physiologically acceptable salt thereof.

2. The method as defined by claim 1, wherein $R_1$ in formula (I) is a hydrogen atom or a methyl or ethyl radical.

3. The method as defined by claim 2, wherein $R_1$ in formula (I) is a hydrogen atom.

4. The method as defined by claim 1, wherein $R_1$ in formula (I) is a hydrogen atom or a methyl radical.

5. The method as defined by claim 4, wherein $R_1$ in formula (I) is a hydrogen atom.

6. The method as defined by claims 2, wherein $R_2$ in formula (I) is a hydrogen atom or a methyl radical.

7. The method as defined by claim 1, said at least one indolecarboxylic acid compound of formula (I), or derivative thereof, being selected from 4,6-dimethoxyindole-2-carboxylic acid, methyl 4,6-dimethoxyindole-2-carboxylate, N-methyl-4,6-dimethoxyindole-2-carboxylic acid, methyl N-methyl-4,6-dimethoxyindole-2-carboxylate or N-ethyl-4,6-dimethoxyindole-2-carboxylic acid.

8. The method as defined by claim 7, wherein said at least one indolecarboxylic acid compound of formula (I), or derivative thereof, is 4,6-dimethoxyindole-2-carboxylic acid or a mixture of 4,6-dimethoxyindole-2-carboxylic acid and at least one compound selected from methyl 4,6-dimethoxyindole-2-carboxylate, N-methyl-4,6-dimethoxyindole-2-carboxylic acid, methyl N-methyl-4,6-dimethoxyindole-2-carboxylate or N-ethyl-4,6-dimethoxyindole-2-carboxylic acid.

9. A topically applicable cosmetic or dermatological composition for inducing or stimulating mammalian hair growth and/or retarding mammalian hair loss, comprising
  a cosmetically or therapeutically effective amount of at least one indolecarboxylic acid compound or ester or salt thereof, said at least one indolecarboxylic acid compound having the structural formula (I):

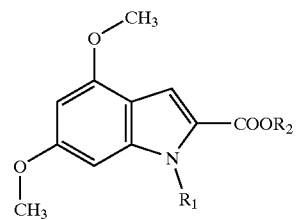

(I)

in which $R_1$ and $R_2$, which may be identical or different, are each a hydrogen atom; a $C_1$–$C_6$ alkyl radical, optionally substituted with an —OH, —$NHR_3$, —SH, —COOH or —$COOR_3$ radical, wherein $R_3$ is a linear or branched $C_1$–$C_4$ alkyl radical; a $C_7$–$C_{12}$ aralkyl radical; or a radical —$CHR_4R_5$ wherein $R_4$ and $R_5$, which may be identical or different, are each a hydrogen atom, an optionally substituted phenyl radical, or a 5- or 6-membered heterocycle; or an acylated derivative or physiologically acceptable salt thereof; and
  a physiologically acceptable medium;
  wherein said physiologically acceptable medium is anhydrous or aqueous, and said anhydrous medium is a solvent selected from among $C_2$–$C_4$ lower alcohols, alkylene glycol alkyl ethers or dialkylene glycol alkyl ethers, the alkyl or alkylene radicals of which have from 1 to 6 carbon atoms; and
  said at least one indolecarboxylic acid compound or ester or salt thereof is formulated into a topically acceptable, cosmetically or dermatologically acceptable vehicle, diluent or carrier therefor.

10. The cosmetic or dermatological composition as defined by claim 9, comprising from 0.3% to 30% by weight of said at least one compound having the structural formula (I).

11. The cosmetic or dermatological composition as defined by claim 10, comprising from 0.5% to 20% by weight of said at least one compound having the structural formula (I).

12. The cosmetic or dermatological composition as defined by claim 9, further comprising an aqueous or anhydrous medium, milk, ointment, emulsion, gel, cream, liposomal form, shampoo or aerosol.

13. The cosmetic or dermatological composition as defined by claim 9, further comprising at least one nicotinic acid ester, 2,4-diamino-6-piperidinopyrimidine 3-oxide, agent for promoting hair regrowth other than said at least one indolecarboxylic compound, antibacterial agent, calcium antagonist, hormone, anti-inflammatory agent, anti-androgenic agent, 5α-reductase inhibitor, potassium agonist, dioxide, spiroxazone, phospholipid, salicyclic acid or an alkyl derivative thereof bearing an alkyl radical of from 2 to 12 carbon atoms in position 5 of the benzene ring, hydroxycarboxylic or ketocarboxylic acid or ester thereof, lactone or salt thereof, anthralin, carotenoid, eicosatetraenoic or eicosatrienoic aid or ester or amide thereof, vitamin D, or extract of plant or bacterial origin.

14. The method as defined by claim 1, wherein formula (I), $R_1$ is a $C_1$–$C_6$ alkyl radical, optionally substituted with an —OH, —$NHR_3$, —SH, —COOH or —$COOR_3$ radical, wherein $R_3$ is a linear or branched $C_1$–$C_4$ alkyl radical; a $C_7$–$C_{12}$ aralkyl radical; or a radical —$CHR_4R_5$ wherein $R_4$ and $R_5$, which may be identical or different, are each a hydrogen atom, an optionally substituted phenyl radical, or a 5- or 6-membered heterocycle; and $R_2$ is a hydrogen atom, a $C_1$–$C_6$ alkyl radical, optionally substituted with an —OH, —$NHR_3$, —SH, —COOH or —$COOR_3$ radical, wherein $R_3$ is a linear or branched $C_1$–$C_4$ alkyl radical; a $C_7$–$C_{12}$ aralkyl radical; or a radical—$CHR_4R_5$ wherein $R_4$ and $R_5$, which may be identical or different, are each a hydrogen atom, an optionally substituted phenyl radical, or a 5- or 6-membered heterocycle.

15. The method as defined by claim 1, wherein formula (I), $R_1$ is a $C_1$–$C_6$ alkyl radical, optionally substituted with an —OH, —$NHR_3$, —SH, —COOH or —$COOR_3$ radical, wherein $R_3$ is a linear or branched $C_1$–$C_4$ alkyl radical; a $C_7$–$C_{12}$ aralkyl radical; or a radical —$CHR_4R_5$ wherein $R_4$ and $R_5$, which may be identical or different, are each a hydrogen atom, an optionally substituted phenyl radical, or a 5- or 6-membered heterocycle; and $R_2$ is a hydrogen atom or a methyl radical.

16. The method as defined by claim 1, wherein formula (I), $R_1$ is a hydrogen atom, a $C_1$–$C_6$ alkyl radical, optionally substituted with an —OH, —$NHR_3$, —SH, —COOH or —$COOR_3$ radical, wherein $R_3$ is a linear or branched $C_1$–$C_4$ alkyl radical; a $C_7$–$C_{12}$ aralkyl radical; or a radical —$CHR_4R_5$ wherein $R_4$ and $R_5$, which may be identical or different, are each a hydrogen atom, an optionally substituted phenyl radical, or a 5- or 6-membered heterocycle; and $R_2$ is a $C_2$–$C_6$ alkyl radical, optionally substituted with an —OH, —$NHR_3$, —SH, —COOH or —$COOR_3$ radical, wherein $R_3$ is a linear or branched $C_1$–$C_4$ alkyl radical; a $C_7$–$C_{12}$ aralkyl radical; or a radical —$CHR_4R_5$ wherein $R_4$ and $R_5$, which may be identical or different, are each a hydrogen atom, an optionally substituted phenyl radical, or a 5- or 6-membered heterocycle.

17. The method as defined by claim 1, wherein formula (I), $R_1$ is a hydrogen atom and $R_2$ is a $C_2$–$C_6$ alkyl radical, optionally substituted with an —OH, —$NHR_3$, —SH, —COOH or —$COOR_3$ radical, wherein $R_3$ is a linear or branched $C_1$–$C_4$ alkyl radical; a $C_7$–$C_{12}$ aralkyl radical; or a radical —$CHR_4R_5$ wherein $R_4$ and $R_5$, which may be identical or different, are each a hydrogen atom, an optionally substituted phenyl radical, or a 5- or 6-membered heterocycle.

18. The cosmetic or dermatological composition as defined by claim 9, wherein formula (I), $R_1$ is a $C_1$–$C_6$ alkyl radical, optionally substituted with an —OH, —$NHR_3$, —SH, —COOH or —$COOR_3$ radical, wherein $R_3$ is a linear or branched $C_1$–$C_4$ alkyl radical; a $C_7$–$C_{12}$ aralkyl radical; or a radical —$CHR_4R_5$ wherein $R_4$ and $R_5$, which may be identical or different, are each a hydrogen atom, an optionally substituted phenyl radical, or a 5- or 6-membered heterocycle; and $R_2$ is a hydrogen atom, a $C_1$–$C_6$ alkyl radical, optionally substituted with an —OH, —$NHR_3$, —SH, —COOH or —$COOR_3$ radical, wherein $R_3$ is a linear or branched $C_1$–$C_4$ alkyl radical; a $C_7$–$C_{12}$ aralkyl radical; or a radical —$CHR_4R_5$ wherein $R_4$ and $R_5$, which may be identical or different, are each a hydrogen atom, an optionally substituted phenyl radical, or a 5- or 6-membered heterocycle.

19. The cosmetic or dermatological composition as defined by claim 9, wherein formula (I), $R_1$ is a $C_1$–$C_6$ alkyl radical, optionally substituted with an —OH, —$NHR_3$, —SH, —COOH or —$COOR_3$ radical, wherein $R_3$ is a linear or branched $C_1$–$C_4$ alkyl radical; a $C_7$–$C_{12}$ aralkyl radical; or a radical —$CHR_4R_5$ wherein $R_4$ and $R_5$, which may be identical or different, are each a hydrogen atom, an optionally substituted phenyl radical, or a 5- or 6-membered heterocycle; and $R_2$ is a hydrogen atom or a methyl radical.

20. The cosmetic or dermatological composition as defined by claim 9, wherein formula (I), $R_1$ is a hydrogen atom, a $C_1$–$C_6$ alkyl radical, optionally substituted with an —OH, —$NHR_3$, —SH, —COOH or —$COOR_3$ radical, wherein $R_3$ is a linear or branched $C_1$–$C_4$ alkyl radical; a $C_7$–$C_{12}$ aralkyl radical; or a radical —$CHR_4R_5$ wherein $R_4$ and $R_5$, which may be identical or different, are each a hydrogen atom, an optionally substituted phenyl radical, or a 5- or 6-membered heterocycle; and $R_2$ is a $C_2$–$C_6$ alkyl radical, optionally substituted with an —OH, —$NHR_3$, —SH, —COOH or —$COOR_3$ radical, wherein $R_3$ is a linear or branched $C_1$–$C_4$ alkyl radical; a $C_7$–$C_{12}$ aralkyl radical; or a radical —$CHR_4R_5$ wherein $R_4$ and $R_5$, which may be identical or different, are each a hydrogen atom, an optionally substituted phenyl radical, or a 5- or 6-membered heterocycle.

21. The cosmetic or dermatological composition as defined by claim 9, wherein formula (I), $R_1$ is a hydrogen, a C–$C_6$ alkyl radical, optionally substituted with an —OH, —$NHR_3$, —SH, —COOH or —$COOR_3$ radical, wherein $R_3$ is a linear or branched $C_1$–$C_4$ alkyl radical; a $C_7$–$C_{12}$ aralkyl radical; or a radical —$CHR_4R_5$ wherein $R_4$ and $R_5$, which may be identical or different, are each a hydrogen atom, an optionally substituted phenyl radical, or a 5- or 6-membered heterocycle; and $R_2$ is a $C_2$–$C_6$ alkyl radical, optionally substituted with an —OH, —$NHR_3$, —SH, —COOH or —$COOR_3$ radical, wherein $R_3$ is a linear or branched $C_1$–$C_4$ alkyl radical; a $C_7$–$C_{12}$ aralkyl radical; or a radical —$CHR_4R_5$ wherein $R_4$ and $R_5$, which may be identical or different, are each a hydrogen atom, an optionally substituted phenyl radical, or a 5- or 6-membered heterocycle.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: primer used to obtain the 5 alpha-reductase I
      cDNA

<400> SEQUENCE: 1
cccagccctg gcgatggcaa c                                              21

<210> SEQ ID NO 2
<211> LENGTH: 22
<212> TYPE: DNA
<213> ORGANISM: Artificial Sequence
<220> FEATURE:
<223> OTHER INFORMATION: primer used to obtain the 5 alpha-reductase I
      cDNA

<400> SEQUENCE: 2
ggatattcaa cctccatttc ag                                             22

<210> SEQ ID NO 3
<211> LENGTH: 17
<212> TYPE: DNA
<213> ORGANISM: Artificial Sequence
<220> FEATURE:
<223> OTHER INFORMATION: primer used to obtain the 5 alpha-reductase II
      cDNA
```

```
-continued

<400> SEQUENCE: 3
gcgatgcagg ttcagtg                                              17

<210> SEQ ID NO 4
<211> LENGTH: 17
<212> TYPE: DNA
<213> ORGANISM: Artificial Sequence
<220> FEATURE:
<223> OTHER INFORMATION: primer used to obtain the 5 alpha-reductase II
      cDNA

<400> SEQUENCE: 4
attgtgggag ctctgct                                              17
```